United States Patent [19]

Weinblatt

[11] Patent Number: 4,837,851

[45] Date of Patent: Jun. 6, 1989

[54] MONITORING TECHNIQUE FOR DETERMINING WHAT LOCATION WITHIN A PREDETERMINED AREA IS BEING VIEWED BY A PERSON

[76] Inventor: Lee S. Weinblatt, 797 Winthrop Rd., Teaneck, N.J. 07666

[21] Appl. No.: 90,458

[22] Filed: Aug. 28, 1987

[51] Int. Cl.[4] .................... H04B 17/00; H04B 1/34; G08B 5/22

[52] U.S. Cl. .................... 455/67; 455/100; 340/825.72; 340/825.36

[58] Field of Search .................... 455/40, 67, 100; 340/825.72, 825.69, 825.49, 825.36, 825.54, 825.19; 342/367

[56] References Cited

U.S. PATENT DOCUMENTS

| | | | |
|---|---|---|---|
| 3,947,832 | 3/1976 | Rösgen et al. | 455/40 X |
| 3,968,435 | 7/1976 | Stover | 455/100 |
| 4,225,953 | 9/1980 | Simon et al. | 340/825.49 X |
| 4,275,385 | 1/1981 | White | 340/825.49 |
| 4,491,971 | 1/1985 | Webb et al. | 455/100 |
| 4,495,496 | 1/1985 | Miller, III | 340/825.54 |

Primary Examiner—Robert L. Griffin
Assistant Examiner—Ralph E. Smith
Attorney, Agent, or Firm—Frishauf, Holtz, Goodman & Woodward

[57] ABSTRACT

A technique for monitoring the reactions of a person exposed to a scene to determine the locations within such scene which attract the person's attention. A portable unit is mounted on the person's head by way of, for example, a set of earphones. A directional transmitter in the portable unit is aimed in the direction of the person's line of sight. Distributed throughout the scene are receivers located at selected points. When the person looks in the direction of one of these receivers, the emitted signal is detected by one of the receivers. An electronic memory stores the detected signal to indicate which of the receivers, and therefore which scene location, was being viewed.

27 Claims, 1 Drawing Sheet

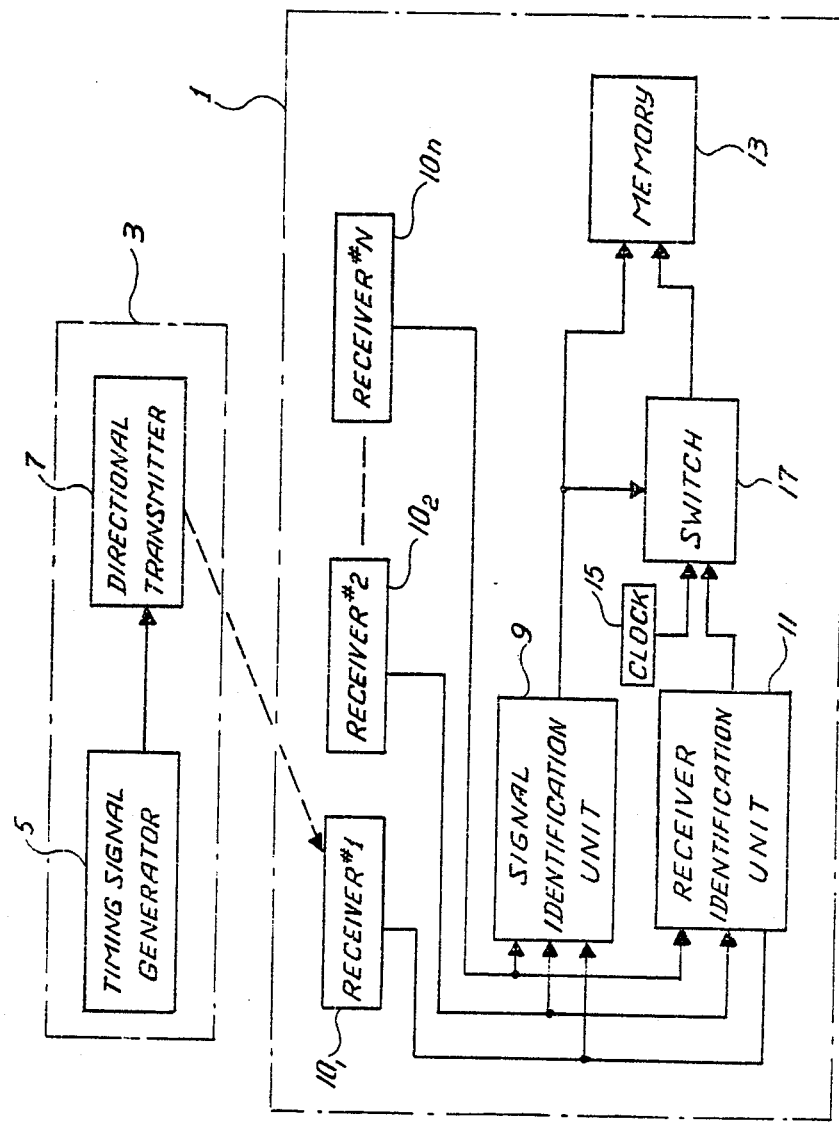

MONITORING TECHNIQUE FOR DETERMINING WHAT LOCATION WITHIN A PREDETERMINED AREA IS BEING VIEWED BY A PERSON

BACKGROUND OF THE INVENTION

The present invention is directed to a technique for monitoring the reactions of a person exposed to a scene and, more particularly, to determine the locations within such scene which attract the person's attention sufficiently to hold his gaze.

In a number of commercial applications it is beneficial to monitor the reactions of an individual person selected to be a test subject when exposed to a predetermined scene. The scene can be, for example, a display in a department store, a shelf in a supermarket, or even a prototype version of an automobile. Each of these examples contains items or features which have been carefully designed to attract the attention of the consumer. For example, when a number of products are competing with each other to be purchased by the consumer, the one which stands out and is most effective in gaining the attention of the consumer may also be the one most likely to be purchased. Consequently, a test of this nature can be revealing in assessing whether, for example, a package which has been designed to stand out does in fact do so. This also applies to the design of an automobile because its shape and features should be pleasing if the consumer is to be sufficiently attracted to purchase it. Results obtained with this test can provide feedback as to whether the various parts of the automobile attract the attention of the test subject sufficiently for him to rest his gaze momentarily on at least a particular one or whether they make little or no impression at all in which case his gaze will simply summarily pass over it. Many other applications of this nature exist which can benefit from information indicative of the extent to which particular elements attract the attention of a test subject. In order to implement such a technique, an approach must be provided which accurately determines the position or positions within a certain viewing area, or scene, on which the test subject's gaze rests.

A number of techniques exist for monitoring the eye movements of a viewer which have the object of determining the location at which his view was directed. One type of such apparatus is generically known as an eye movement monitoring system utilizing head-mounted detectors aimed at the viewer's eye. However, these are relatively complex because the viewer's eye movements must accurately be associated or correlated with the scene being viewed. The calibration to do this is relatively time consuming and is subject to change and error. Also, the equipment and processing techniques are relatively awkward and complex. Moreover, the equipment can be expensive. Furthermore, some of these approaches require a heavy and bulky headgear which is inconvenient to use.

Another disadvantage of such known monitoring techniques is the awareness of the person that his reactions are being tested. A person may not react naturally when he knows that his actions are being monitored and recorded. The test results might, therefore, be somewhat skewed.

SUMMARY OF THE INVENTION

It is the primary object of present invention to provide a technique for monitoring the viewing of a predetermined area by a person to identify the locations which he finds attractive.

Another object of the present invention is to provide such a viewing monitoring apparatus, which is accurate and yet relatively simple and inexpensive.

A further object of the present invention is to provide such a viewing monitoring apparatus which is convenient to use and operate.

Yet another object of the present invention is to provide such a viewing monitoring apparatus capable of monitoring the reactions of a person without the person's knowledge that this is being done.

These and other objects of the present invention are attained by an apparatus for identifying what is being looked at by an individual person within a predetermined area, comprising a portable unit adapted to be worn by the person and including a transmitter means for emitting a viewer signal in substantially the direction in which the person is looking. A stationary unit is adapted to be placed in a selected portion of the predetermined area. It includes a receiver means for detecting the viewer signal to generate a receiver output signal. A memory means is coupled to the receiver means for storing a record signal representative of the receiver output signal.

Another aspect of the invention is directed to an apparatus for determining a location within a predetermined viewing area which is being looked at by an individual person, comprising a portable unit adapted to be worn by the person and including a transmitter means for emitting a viewer signal in substantially the direction in which the person is looking. A plurality of receiver means is located, respectively, in selected locations within the predetermined area for detecting the viewer signal to generate a receiver output signal. A memory means is coupled to the plurality of receiver means for storing a record signal identifying the one of the plurality of receiver means which generates a receiver output signal in response to said viewer signal.

A further aspect of the present invention is directed to a method for identifying what is being looked at by an individual person within a predetermined area, comprising the steps of mounting a portable unit including a transmitter means for emitting a viewer signal to be worn by the person to aim the viewer signal in substantially the direction in which the person is looking, providing a stationary unit in a selected portion of the predetermined area for detecting the viewer signal to generate a receiver output signal, and storing a record signal representative of the receiver output signal.

Yet another aspect of the present invention is directed to a method for determining a location within a predetermined viewing area which is being looked at by an individual person, comprising the steps of mounting a portable unit including a transmitter means for emitting a viewer signal to be worn by the person to aim the viewer signal in substantially the direction in which the person is looking, providing a plurality of receiver means located, respectively, in selected locations within the predetermined area for detecting the viewer signal to generate a receiver output signal, and storing a record signal identifying the one of the plurality of receiver means which generates a receiver output signal in response to the viewer signal.

BRIEF DESCRIPTION OF THE DRAWING

The drawing depicts a schematic block diagram of a circuit in accordance with the principles of the invention, with a signal being emitted toward receiver #1.

DETAILED DESCRIPTION OF THE PREFERRED EMBODIMENT

In the following discussion, it is presumed that an individual person has been selected as a test subject whose reactions to a certain scene are to be monitored. The scene, or predetermined viewing area, as it is used throughout this specification, refers to a structure or items or features of interest to those conducting the test. For example, as explained above, the scene, or predetermined area, can include a shelf display in a supermarket or a prototype of a new automobile. The scene includes certain features the human reactions to which are of particular interest. For example, in the supermarket shelf display example, at least one of the displayed products may have been the object of conducting the test. Consequently, these particular boxes must be monitored. Likewise, in the prototype version of an automobile example, it may be advantageous and beneficial to determine whether some feature, such as the grill, headlights, taillights, etc. hold the attention of the test subject. Consequently, the invention is based on the presumption that at least one of such locations or positions within the predetermined area exists which is to be monitored.

In order to monitor a number of such locations, a stationary unit 1 is provided which operates in conjunction with a portable unit 3. A plurality of receivers is used in stationary unit 1, with one being installed in each location. Receivers $10_1, 10_2, \ldots 10_n$ are shown in the figure as being utilized for this purpose. Each receiver is mounted on or is in some way clearly associated with a feature the monitoring of which is desired so that the receiver generates a receiver output signal when the test subject is looking at its corresponding feature.

Portable unit 3 includes timing signal generator 5 and directional transmitter 7. Transmitter 7 can, for example, generate an infrared signal. Such a transmitter is conventional and well known in the art. Consequently, it is not deemed necessary to provide its details. It is desirable to provide transmitter 7 with a relatively narrow beam spread so that it actuates one of the receivers $10_1-10_n$ only when transmitter 7 is aimed substantially directly at it. Otherwise, of course, the meaningfulness of the test results would be obscured if the transmitter output had a spread such as to actuate more than one receiver at a time. Obtaining transmitter directionality is also old and well known in the art. For example, a tube (not shown) can be placed in front of the transmitter so that only those signal beams aimed substantially axially of the tube will be emitted. The narrower the tube, the more directional is the transmitter output signal.

The function of timing signal generator 5 is to repeatedly actuate the emission of a transmitter output signal. Generator 5 can, for example, be simply in the nature of an oscillator operating at a designated frequency.

Portable unit 3 is configured to be worn on the head of the test subject. Moreover, it is designed so that it can be fitted onto the head of the test subject in such a manner that, when appropriately placed, the transmitter output signal is emitted in a direction which substantially coincides with the line of gaze of the test subject's eyes, assuming that the eyes are directed toward the front. It has been found that in looking at objects which are relatively far away, this is a reliable assumption to make because the test subject is more likely to turn the head than to rotate the eyes.

Transmitter 7 includes means for emitting a unique code which can be used to identify a particular viewer, or merely to separate one test subject from another so that the results obtained from many persons are not merely lumped together. Also, as explained below, it may be advantageous to retain data in a manner which identifies the test subject, if not by name then by various characteristics. It may be significant to know what different individual test subjects looked at rather than to group them all together. Consequently, the output of transmitter 7 can be considered as being a unique viewer signal. Further operational details are provided below which will make this point even clearer.

Since it is important to properly mount portable unit 3 on the head of the test subject, a suitable means for this purpose must be provided. One example which can be used is a set of earphones (not shown) to which the directional transmitter 7 is attached. Another possibility is a clip-on apparatus designed to be easily secured to the frame of a pair of eyeglasses. It is respectfully submitted that no structural details need to be provided. However, an example of the former can be found in U.S. Pat. Applicatiion No. 827,760 filed Feb. 7, 1986. An example of the latter can be found in U.S. Pat. No. 4,649,434. The contents of both are hereby incorporated by reference. The utilization of earphones is preferred for reasons explained below.

Stationary unit 1 includes receivers $10_1-10_n$ which are responsive to the unique viewer signal emitted by directional transmitter 7. As explained above, each of these receivers is placed at a particular location. Stationary unit 1 also includes signal identification unit 9 which responds via the receivers to the unique viewer signal emitted by directional transmitter 7. For example, signal identification unit 9, in an analog embodiment, can be a narrow band pass filter, with the unique viewer signal being a signal within that band pass. In a digital embodiment, the unique viewer signal is digitally coded, with that code being compared with a stored code in signal identification unit 9 to find a match therebetween. Such circuits are conventional and well known in the art, and it is not considered necessary to provide further details thereof.

Signal identification unit 9 can be provided with only one unique viewer signal which corresponds to that assigned to the individual being tested at that particular time. Alternatively, a plurality of unique viewer signals can be stored in signal identification unit 9 which correspond to all of the unique viewer signals assigned to all of the persons acting as test subjects in a particular test session. An advantage of the former is that the possibility of a spurious signal being detected is minimized. An advantage of the latter is that the signal identification unit 9 need not be reset for each individual test subject.

All of receivers $10_1-10_n$ are connected to signal identification unit 9. Whichever one of these receivers detects the unique viewer signal from transmitter 7, its receiver output signal is input to signal identification unit 9.

Stationary unit 1 also includes a receiver identification unit 11 which serves to identify the particular one of receivers $10_1-10_n$ which detected the unique viewer signal from directional transmitter 7. Receiver identification unit 11 can take any operative form ranging from a relatively simple diode matrix to a digital device responding to unique codes provided for each of receivers $10_1$-$10_n$. The particular configuration of unit 11 does not form a part of the present invention in that a device of this sort is conventional and well known in the art. Accordingly, it is not deemed necessary to provide further details thereof.

The outputs of signal identification unit 9 and receiver identification unit 11 are input to an electronic memory 13. The receiver identification unit 11 provides an input signal to memory 13 for enabling it to retain the identity of the particular receiver which detected the unique viewer signal emitted by transmitter 7. Consequently, by knowing where each of the receiver $10_1$-$10_n$ is physically located in the predetermined area, identifying a particular receiver inherently also identifies its location. Memory 13 thus stores each occurrence of a signal from unit 11 along with the identity of the receiver. Storing the output of signal identification unit 9 in memory 13 also provides information on which of the individual test subjects is associated with an output from an identified one of receivers $10_1$-$10_n$. Consequently, all of the reactions of a particular test subject can be set apart and analyzed as a group separate and apart from the test results obtained with another person.

Stationary unit 1 further includes a clock 15 to provide time of day information. This time information is also stored in memory 13. Thus, as signals are stored in memory 13 from units 9 and 11, the time of occurrence is also stored. One benefit of this arrangement is to provide the capability to analyze the total amount of time at which a particular location was being looked at. This could be considered indicative of the level or degree of interest of that particular location to the test subject.

It is desired to store information in memory 13 only when signal identification unit 9 detects a unique viewer signal. Otherwise, all signals detected by a receiver would be stored even those unrelated to the test, which is not a useful result. Consequently, switch 17 is utilized. The inputs of switch 17 are connected the outputs of receiver identification unit 11 and clock 15. Switch 17 is normally open so that signals from receiver identification unit 11 and clock 15 do not pass to memory 13. The actuating input of switch 17 is connected to the output of signal identification unit 9. In response to an output signal from unit 9, switch 17 is closed to pass to memory 13 the output signals from receiver identification unit 11 and clock 15. In addition, the output of signal identification unit 9 is also connected to memroy 13 for retention therein.

It is common for a person when exposed to a scene to do a very fast scan of substantially all of it to quickly grasp what it is about before settling down to a more careful and thorough study of it. In doing that quick scan, it is likely that the person's gaze will hit at least some of receivers $10_1$-$10_n$ even though none of the features have been effective yet at that time to hold his attention. Consequently, such a reading might be considered spurious if detected and recorded. In order to avoid this situation, the apparatus of the present invention might be provided with a time threshold circuit which will inhibit any processing and/or recordal of a viewer signal if the gaze of the test subject does not rest on that particular location for a minimum amount of time. A suitable time threshold circuit can be incorporated into receivers $10_1$-$10_n$ or into signal identification unit 9, for example. No further details are believed to be necessary because one with ordinary skill in the art is well acquainted with such devices.

Suitable apparatus can be used to retrieve information from memory 13 so that an analysis thereof can be performed. This can be done by simply printing the information for the purpose of analyzing it normally or outputting it electronically to a computer for an automated analysis.

In operation, portable unit 3 is properly affixed to the head of the individual test subject so that the signal emitted by directional transmitter 7 is aimed to be substantially coincident with the direction of gaze of the test subject when looking forward. Timing signal generator 5 periodically actuates an emission of the unique viewer signal from directional transmitter 7.

The unique viewer signal from directional transmitter 7 is detected by whichever one of receivers $10_1$-$10_n$ is located at the position being viewed by the test subject. That particular receiver generates a receiver output signal to both signal identification unit 9 as well as receiver identification unit 11. When a unique viewer signal is identified by signal identification unit 9, it generates a signal both to memory 13 as well as to switch 17. Consequently, switch 17 is closed. Receiver identification unit 11 is responsive to the output of the particular one of receivers $10_1$-$10_n$ which detected the unique viewer signal from directional transmitter 7. Receiver identification unit 11 identifies that receiver and sends its corresponding output signal via switch 17 to memory 13. Also, clock 15 provides an input to memory 13 indicative of the time in which a particular event occured, as well as its duration.

The information contained in memory 13 as a result of the processing provided by the various components of stationary unit 1 can be highly advantageous and revealing. If a unique viewer signal is identified with a particular test subject, a statistical analysis can be obtained utilizing the characteristics of each test subject. For example, reactions can be obtained by geographic location, age, sex, economic status, education, etc. The products can then be modified so as to be geared to a particular category of consumer. Also, by storing time information with the assistance of clock 15, a relative analysis can be performed to compare with each other the various locations in the predetermined area in terms of viewer interest. For example, it may be that a particular test subject was not attracted to anything in the scene to which he was exposed. Consequently, those results can be tossed out as either being inaccurate due to faulty equipment or because the particular test subject was not attentive. Likewise, such timing information could serve to identify characteristics, features, or the like which are outstandingly attractive or outstandingly poor so that the necessary conclusions can be drawn.

With portable unit 3 being secured to earphones worn by the individual undergoing the test, a natural mode of conduct by that person can be sustained. The earphones can be advantageously utilized to prevent the person from knowing that he is participating in a test of the kind in which his direct reactions are being monitored. For example, a volunteer can be asked to walk through an automobile showroom or a supermarket so that his collective impressions can later be sought. He is handed a pair of earphones through which information, instructions, descriptions, etc. are provided. However, the person is not aware that the portable unit 3 on the earphones is monitoring his reactions. Consequently, the person is more likely to be at ease and to act naturally. This can be a significant factor in enhancing the accuracy of such test results.

Although a preferred embodiment of the present invention has been discussed in detail above, various modifications thereto will be readily apparent to one with ordinary skill in the arts. For example, switch 17 can be eliminated and the output from signal identification unit 9 can be connected to clock 15 and receiver unit 11 to serve as an actuating signal. In other words, the outputs from clock 15 and receiver identification unit 11 will be inhibited unless such actuation signal is provided. Also, receiver identification unit 11 can be eliminated and, instead, an identifying signal can be provided directly from each of receivers $10_1$–$10_n$ to memory 13. With this arrangement, the memory 13 would be inhibited from storing information unless an actuating signal is received from signal identification unit 9. Furthermore, clock 15 need not provide a time of day. Instead, all that it is required to do is to provide a regular timing signal to obtain an indication of a time interval rather than the time of day. In addition a transmitter and receivers responsive to a signal other than of the infrared type can be used as well. These and other such modifications are all intended to be included within the scope of the present invention as defined by the following claims:

I claim:

1. An apparatus for determining what portion of a predetermined area is being looked at by an individual person, comprising:
   a portable unit including means for securing such unit so as to be worn by a person, and a transmitter means for emitting a viewer signal in substantially the direction in which said person is looking;
   a stationary unit located in a selected portion of said predetermined area and including a receiver means for detecting said viewer signal to generate a receiver output signal;
   wherein said transmitter means includes directional means for narrowing the spread of said viewer signal to direct said viewer signal in substantially only the direction in which said person is looking.

2. The apparatus of claim 1 further comprising mounting means for retaining said transmitter means on the head of said person to position said directional means such that the viewer signal is emitted only in substantially the direction in which said person is looking.

3. The apparatus of claim 2, wherein said transmitter means emits a unique viewer signal.

4. The apparatus of claim 3, wherein said stationary unit further comprises a signal identification means coupled between said receiver means and said memory means for generating a viewer identification signal in response only to a receiver output signal which is the unique viewer signal, said memory means storing a record signal only in response to said viewer identification signal.

5. The apparatus of claim 4, further comprising a clock means coupled to the memory means, said memory storing a time signal from said clock means along with said record signal.

6. The apparatus of claim 5, wherein said apparatus comprises a plurality of receiver means located at respective selected portions of said predetermined area, and further comprising a receiver identification unit for identifying which one of said plurality of receiver means generates a receiver output signal in response to a viewer signal, said memory means including means to store the record signal along with identification of said one of the plurality of receiver means.

7. The apparatus of claim 6, further comprising a timing means coupled to said transmitter means for actuating the periodic transmission of said viewer signal.

8. The apparatus of claim 1, wherein said transmitter means emits a unique viewer signal.

9. The apparatus of claim 8, wherein said stationary unit further comprises a signal identification means coupled between said receiver means and said memory means for generating a viewer identification signal in response only to a receiver output signal which is the unique viewer signal, said memory means storing a record signal only in response to said viewer identification signal.

10. The apparatus of claim 1, further comprising a clock means coupled to the memory means, said memory means storing a time signal from said clock means along with said record signal.

11. The apparatus of claim 1, wherein said apparatus comprises a plurality of receiver means located at respective selected portions of said predetermined area, and further comprising a receiver identification unit for identifying which one of said plurality of receiver means generates a receiver output signal in response to a viewer signal, said memory means including means to store the record signal along with identification of said one of the plurality of receiver means.

12. The apparatus of claim 1, further comprising a timing means coupled to said transmitter means for actuating the periodic transmission of said viewer signal.

13. The apparatus of claim 1, further comprising a switch means having its input coupled to the output of said receiver means and responsive to said viewer identification signal to pass the receiver output signal to said memory means only when a unique viewer signal is detected.

14. An apparatus for determining a location within a predetermined viewing area which is being looked at by an individual person, comprising:
    a portable unit including means for securing such unit so as to be worn by a person, and a transmitter means for emitting a viewer signal in substantially the direction in which said person is looking;
    a plurality of receiver means located, respectively in selected locations within said predetermined area for detecting said viewer signal to generate a receiver output signal; and
    memory means coupled to said plurality of receiver means for storing a record signal identifying the one of said plurality of receiver means which generates a receiver output signal in response to said viewer signal;
    wherein said transmitter means includes directional means for narrowing the spread of said viewer signal to direct said viewer signal in substantially only the direction in which said person is looking.

15. The apparatus of claim 14 further comprising mounting means for retaining said transmitter means on the head of said person to position said directional means such that the viewer signal is emitted only in substantially the direction in which said person is looking.

16. The apparatus of claim 15, further comprising a receiver identification unit for identifying which one of said plurality of receiver means generates a receiver output signal in response to a viewer signal, said memory means including means to store the record signal along with identification of said one of the plurality of receiver means.

17. The apparatus of claim 16, further comprising a clock means coupled to the memory means, said memory storing a time signal from said clock means along with said record signal.

18. The apparatus of claim 17, further comprising a timing means coupled to said transmitter means for actuating the periodic transmission of said viewer signal.

19. The apparatus of claim 14, further comprising a receiver identification unit for identifying which one of said plurality of receiver means generates a receiver output signal in response to a viewer signal, said memory means including means to store the record signal along with identification of said one of the plurality of receiver means.

20. The apparatus of claim 14, further comprising a clock means coupled to the memory means, said memory means storing a time signal from said clock means along with said record signal.

21. The apparatus of claim 14, further comprising a timing means coupled to said transmitter means for actuating the periodic transmission of said viewer signal.

22. Method for determining what portion of a predetermined area is being looked at by an individual person, comprising the steps of:
mounting a portable unit including a transmitter means to be worn by the person for emitting a viewer signal;
narrowing the spread of said viewer signal to aim the viewer signal in substantially only the direction in which said person is looking;
providing a stationary unit in a selected portion of said predetermined area for detecting said viewer signal to generate a receiver output signal; and
storing a record signal representative of said receiver output signal.

23. Method for determining a location within a predetermined viewing area which is being looked at by an individual person, comprising the steps of:
mounting a portable unit including a transmitter means to be worn by the person for emitting a viewer signal;
narrowing the spread of said viewer signal to aim the viewer signal in substantially only the direction in which said person is looking;
providing a plurality of receiver means located, respectively, in selected locations within said predetermined area for detecting said viewer signal to generate a receiver output signal; and
storing a record signal identifying the one of said plurality of receiver means which generates a receiver output signal in response to said viewer signal.

24. An apparatus for determining what portion of a predetermined area is being looked at by an individual person, comprising:
a portable unit including means for securing such unit so as to be worn by a person, and a transmitter means for emitting a viewer signal in substantially the direction in which said person is looking;
a stationary unit located in a selected portion of said predetermined area and including a receiver means for detecting said viewer signal to generate a receiver output signal;
memory means coupled to the receiver means for storing a record signal representative of said receiver output signal; and
a clock means coupled to the memory means, said memory means storing a time signal from said clock means along with said record signal.

25. Apparatus for determining what portion of a predetermined area is being looked at by an individual person, comprising:
a portable unit including means for securing such unit so as to be worn by a person, and a transmitter means for emitting a viewer signal in substantially the direction in which said person is looking;
a stationary unit located in a selected portion of said predetermined area and including a receiver means for detecting said viewer signal to generate a receiver output signal;
memory means coupled to the receiver means for storing a record signal representative of said receiver output signal; and
a timing means coupled to said transmitter means for actuating the periodic transmission of said viewer signal.

26. Apparatus for determining a location within a predetermined viewing area which is being looked at by an individual person, comprising:
a portable unit including means for securing such unit so as to be worn by a person, and a transmitter means for emitting a viewer signal in substantially the direction in which said person is looking;
a plurality of receiver means located, respectively, in selected locations within said predetermined area for detecting said viewer signal to generate a receiver output signal;
memory means coupled to said plurality of receiver means for storing a record signal identifying the one of said plurality of receiver means which generates a receiver output signal in response to said viewer signal; and
a clock means coupled to the memory means, said memory means storing a time signal from said clock means along with said record signal.

27. Apparatus for determining a location within a predetermined viewing area which is being looked at by an individual person, comprising:
a portable unit including means for securing such unit so as to be worn by a person, and a transmitter means for emitting a viewer signal in substantially the direction in which said person is looking;
a plurality of receiver means located, respectively, in selected locations within said predetermined area for detecting said viewer signal to generate a receiver output signal;
memory means coupled to said plurality of receiver means for storing a record signal identifying the one of said plurality of receiver means which generates a receiver output signal in response to said viewer signal; and
timing means coupled to said transmitter means for actuating the periodic transmission of said viewer signal.

* * * * *